United States Patent [19]

Alper et al.

[11] Patent Number: 5,149,741
[45] Date of Patent: Sep. 22, 1992

[54] HOT MELT CONSTRUCTION ADHESIVES FOR DISPOSABLE SOFT GOODS

[75] Inventors: Mark D. Alper, New Berlin; Marion M. Myers, Milwaukee, both of Wis.

[73] Assignee: Findley Adhesives, Inc., Wauwatosa, Wis.

[21] Appl. No.: 763,436

[22] Filed: Sep. 20, 1991

Related U.S. Application Data

[63] Continuation-in-part of Ser. No. 383,834, Jul. 21, 1989, abandoned.

[51] Int. Cl.$^5$ .................. C09J 109/06; C09J 125/10; C09J 191/00; C09J 193/00
[52] U.S. Cl. ...................... 525/95; 156/327; 156/334; 524/270; 524/271; 524/272; 524/274; 524/505; 525/98
[58] Field of Search .............. 156/327, 334; 524/270, 524/271, 272, 274, 505; 525/95, 98

[56] References Cited

U.S. PATENT DOCUMENTS

| | | | |
|---|---|---|---|
| 3,238,173 | 3/1966 | Bailey et al. | 524/505 |
| 3,635,861 | 1/1972 | Russell | 525/98 |
| 3,783,072 | 1/1974 | Korpman | 524/505 |
| 3,932,328 | 1/1976 | Korpman | 524/274 |
| 3,932,329 | 1/1976 | Lakshmanan | 524/274 |
| 3,932,330 | 1/1976 | Lakshmanan | 524/271 |
| 3,956,223 | 5/1976 | Chiang et al. | 525/98 |
| 4,136,071 | 1/1979 | Korpman | 524/274 |
| 4,294,936 | 10/1981 | Korpman | 524/271 |
| 4,302,371 | 11/1981 | Matsuo et al. | 524/272 |
| 4,359,551 | 11/1982 | Suda et al. | 524/271 |
| 4,391,949 | 7/1983 | St. Clair | 524/274 |
| 4,419,494 | 12/1983 | Puletti et al. | 525/95 |
| 4,444,953 | 4/1984 | St. Clair | 524/274 |
| 4,526,577 | 7/1985 | Schmidt, Jr. et al. | 604/366 |
| 4,548,988 | 10/1985 | Castelein | 525/98 |
| 4,556,464 | 12/1985 | St. Clair | 525/95 |
| 4,717,749 | 1/1988 | Tang et al. | 525/98 |
| 4,725,641 | 2/1988 | Comert et al. | 524/505 |
| 4,761,341 | 8/1988 | Rosiak et al. | 524/505 |
| 4,785,043 | 11/1988 | Kawai et al. | 524/272 |
| 5,019,071 | 5/1991 | Bany et al. | 524/505 |
| 5,028,646 | 7/1991 | Miller et al. | 524/505 |
| 5,057,571 | 10/1991 | Malcolm et al. | 524/505 |
| 5,079,090 | 1/1992 | Joseph et al. | 525/98 |
| 5,080,978 | 1/1992 | Kulzick et al. | 428/483 |

Primary Examiner—John Kight, III
Assistant Examiner—Rabon Sergent
Attorney, Agent, or Firm—Godfrey & Kahn

[57] ABSTRACT

Hot melt construction adhesives are described which possess superior properties for the construction of disposable soft articles. The adhesive compositions include an SIS copolymer containing at least about 25% styrene, a compatible tackifying resin, a plasticizing oil and an effective amount of a stabilizer.

6 Claims, No Drawings

HOT MELT CONSTRUCTION ADHESIVES FOR DISPOSABLE SOFT GOODS

The present application is a continuation-in-part of application Ser. No. 07/383,834 and which was filed on Jul. 21, 1989, now abandoned.

FIELD OF THE INVENTION

The present invention relates to construction adhesives and more particularly, it relates to new hot melt construction adhesives which find utility in the manufacture of disposable soft goods such as diapers, feminine napkins and the like.

BACKGROUND OF THE INVENTION

The prior art is replete with numerous examples of hot melt adhesives which are employed for the construction of disposable soft goods. Specific applications for these prior art adhesives have included disposable diapers, sanitary napkins, surgical drapes, hospital pads and adult incontinent products to name but a few. Moreover, the prior art methods of application of these prior art adhesives have included, but are not limited to, extrusion (multi-bead or slot), and spray or wheel application systems.

Those skilled in the art will readily recognize that many different polymer bases have been used, heretofore, to formulate hot melt adhesives for the construction of disposable soft goods. In this regard, the first copolymers to be employed were the ethylene vinyl acetate copolymers (EVA) and amorphous polypropylene (APP). While these polymers, when properly blended, provided acceptable adhesion to most substrates, they had several shortcomings which detracted from their usefulness. One of the first shortcomings of these polymers was that they lacked the desired elevated temperature resistance. For example, it is very important that a construction adhesive, for disposable soft goods, maintain its bond, not only at room temperature, but also at elevated temperatures, that is, 100° F., 38° C. This elevated temperature resistance is important because without this characteristic, delamination of the end product occurs if the adhesive bond comes into contact with the user's skin. A second shortcoming of the prior art adhesives which were based in whole or in part on EVA or APP is that these polymers have a tendency to "gel" or otherwise increase in viscosity, or char when subjected to typical commercial application temperatures, that is 300°-350° F. In most instances, this drawback manifests itself in the form of poor application characteristics, such as plugged equipment nozzles. Further, those skilled in the art will recognize that adhesives based upon EVA or APP cannot generally be formulated as multi-purpose adhesive compositions.

As should be understood, multi-purpose adhesive compositions are those adhesives which can be used for more than one application. For example, and in the manufacture of most disposable diapers, today, it should be understood that several different adhesive applications are present. These adhesive applications include, the use of adhesives in construction, that is, bonding the polyethylene to the nonwoven and absorbent pad; on some diapers this adhesive also bonds a colored film in place at the end seals; the use of adhesives for elastic attachment, that is, bonding the elastic material to the polyethylene in either the leg and/or waist area; the use of adhesives for landing strips, that is, bonding a reinforcing layer of polyolefin film to the polyethylene in the area opposite the tape tabs; and the use of core adhesives, that is, applying an adhesive to the absorbent core to increase the strength of the core.

As should be appreciated, multi-purpose adhesive products which can be used for more than one application are desireable inasmuch as they reduce the number of different adhesive products which must be held in a manufacturers inventory. Furthermore, a reduction in the number of adhesive products employed by a manufacturer reduces the likelihood of the wrong adhesive being used during a manufacturing cycle. In addition to the foregoing, the use of a multi-purpose adhesive will, as a general manner, be less costly because of the volume discounts which are generally available when larger quantities of a single adhesive product are purchased.

As discussed earlier, the prior art EVA and APP based adhesive compositions have not generally been compounded, heretofore, to form multi-purpose adhesives with pressure sensitive properties because these formulations were found to be severely compromised as to the strength, and elevated temperature resistance. As should be understood, pressure sensitivity is extremely important to multi-purpose adhesive compositions because a pressure sensitive adhesive will form a bond over a much wider range of application conditions, such as temperature, than a non pressure sensitive adhesive composition.

In addition to the prior art adhesives discussed above, adhesives based on styrene-butadiene-styrene (SBS) block copolymers were suggested for use in the construction of disposable soft goods. An example of these prior art adhesives is disclosed in U.S. Pat. No. 4,526,577. The SBS based adhesive compositions appeared to be improvements over the previously employed adhesives in several important respects, but they also had several drawbacks which also detracted from their usefulness. For example, it was discovered that when an SBS based adhesive composition was left in an adhesive applicator for an extended period of time, it would rapidly increase in viscosity and ultimately gel thereby making it extremely difficult to remove. Furthermore, adhesive compositions based upon SBS copolymers did not appear to have sufficient elevated temperature creep resistance to perform well as an elastic attachment adhesive as compared with adhesive compositions based upon the styrene-isoprene-styrene (SIS) block copolymers of the present invention. Furthermore, many diaper manufacturers have recently added a foamed elastic waistband to their disposable diaper products, and the SBS based adhesive compositions appear completely unacceptable for this particular manufacturing application. This appears to be due to insufficient elevated temperature creep resistance.

Recently, many disposable garment manufacturers have begun to use spray application equipment. In this particular manufacturing equipment, it should be understood that immediately after the adhesive composition is extruded through a nozzle, it is picked up by an air stream which transports the adhesive composition to the desired substrate. As should be understood, this method of applying an adhesive tends to reduce the temperature of the adhesive composition, when compared to other application systems, even if the air stream is heated. In addition to the foregoing, the adhesive composition is substantially elongated by this process, which further increases the cooling effect because the adhesive composition increases in its overall surface area. In some applications, this cooling effect can be exploited. For example, this cooling effect, in spray application systems, can be used to bond substrates together which are very heat sensitive. However, and because of the cooling effect which takes place, it is usually necessary that the adhesive composition have a high degree of pressure sensitivity even when they are cooled by this type of application equipment.

As discussed above, adhesive compositions based upon styrene-isoprene-styrene (SIS) block copolymers have also been used, heretofore, in the construction of disposable soft articles. While these adhesive compositions have been used, they also have had several noteworthy deficiencies which have detracted from their usefulness. For example, adhesive compositions employing previously commercially available SIS copolymers displayed a low modulus and poor elevated temperature resistance even when formulated with various tackifying resins. In an attempt to improve the temperature resistance of the various SIS based compositions, end block reinforcing resins were blended with same. However, these resins appeared to decrease the specific adhesion of the adhesive compositions to polyolefin substrates and also raised the raw material cost of the final adhesive composition inasmuch as these reinforcing resins are generally quite expensive. Moreover, it appeared that, with respect to maintaining any significant degree of elevated temperature resistance, adhesive compositions containing SIS copolymers appeared to require relatively nonpolar tackifying resins, that is, partially or totally hydrogenated resins or aliphatic C-5 resins. However, it became evident following experimentation that resins containing a significant amount of polar or aromatic components tended to associate with the end block of the block copolymer, and thereby decreased the elevated temperature resistance to unacceptable levels. As a result, and when adhesive compositions were compounded using SIS copolymers and these relatively non-functional resins, the resultant adhesive compositions had what was considered, very poor adhesion to polyolefin substrates. While these same adhesive compositions were acceptable for use as elastic attachment adhesives, that is, where a high level of specific adhesion is not generally needed, they further appeared completely unsuitable for use as construction adhesives, that is, where a very high level of specific adhesion to polyolefin substrates was mandatory. Moreover, these same compounds tended to yield products with undesireably high viscosities at application temperatures. As a result of the foregoing, it was believed that adhesive compositions based upon SIS copolymers would not be suitable for use as multi-purpose adhesives.

OBJECTS AND SUMMARY OF THE INVENTION

It is therefore an object of the present invention to provide improved hot melt construction adhesives which are uniquely suited for the manufacture of disposable soft goods.

It is a further object of the present invention to provide hot melt construction adhesives which can be employed as a multi-purpose adhesive, and which further can be applied by utilizing either extrusion or spray techniques, to at least one polyolefin nonwoven substrate, and at least one elastic, polyolefin or nonwoven substrate.

Another object of the present invention is to provide hot melt construction adhesives which have the following composition:
a) about 15 to about 40 parts, by weight, of an S-I-S block copolymer, and wherein S is styrene, and I is isoprene, and wherein the styrene content is about 25% to about 50% of the total weight of the block copolymer;
b) about 40 parts to about 70 parts, by weight, of a compatible tackifying resin;
c) about 5 parts to about 30 parts, by weight, of a plasticizing oil;
d) 0 to about 5 parts, by weight, of a petroleum derived wax; and
e) about 0.1 to about 2 parts, by weight, of a stabilizer.

Another object of the present invention is to provide a hot melt construction adhesive which also can be employed in applications which include landing zones, elastic attachments, elastic foam waistbands or combinations thereof.

Another object of the present invention is to provide hot melt construction adhesives which may be employed as multi-purpose hot melt adhesives for disposable soft goods production and which can be formulated by utilizing styrene-isoprene-styrene block copolymers and which have a significantly higher styrene content than those S-I-S copolymers which were previously commercially available.

Another object of the present invention is to provide hot melt construction adhesives which are formulated into either single or multi-purpose adhesive products without the need of employing the reinforcing resins which were previously considered essential.

Another object of the present invention is to provide hot melt construction adhesives which can be formulated by utilizing functional resins which impart a high degree of specific adhesion to the adhesives, without a simultaneous loss of cohesive strength, either at ambient, or elevated application temperatures.

Still another object of the present invention is to provide hot melt construction adhesives which employ high styrene content S-I-S copolymers, and wherein the adhesive compositions employing same are both low in viscosity, have excellent application characteristics, and are well suited for multi-purpose use as either construction or elastic attachment adhesives, or both.

Another object of the present invention is to provide hot melt construction adhesives which can be formulated from high styrene content S-I-S copolymers and which have enhanced spraying characteristics as compared with adhesive compositions formulated from other copolymer bases.

A further object of the present invention is to provide hot melt construction adhesive compositions wherein the adhesive compositions based upon high styrene content S-I-S block copolymers do not increase in viscosity or gel, even under prolonged heat aging at application temperatures, as do the high styrene content S-B-S based adhesives of the prior art.

Another object of the present invention is to provide hot melt construction adhesive compositions wherein high styrene content, S-I-S copolymers are employed and which make it possible to formulate hot melt pressure sensitive adhesives which possess an excellent balance of high specific adhesion, elevated temperature resistance and acceptable cohesive strength at relatively low viscosities.

A further object of the present invention is to provide hot melt construction adhesive compositions which form strong bonds to polyolefin substrates, elastic materials, that is, natural rubber or Lycra elastic, and tissue and nonwoven substrates.

Still a further object of the present invention is to provide hot melt construction adhesives which have improved creep resistance as compared to the prior art S-I-S based adhesives employed heretofore.

Further objects and advantages are to provide hot melt construction adhesives for the purposes described and which are durable, easy to apply utilizing conventional manufacturing techniques, and which further do not have the numerous shortcomings attributable to the prior art construction adhesives used heretofore.

DESCRIPTION OF THE PREFERRED EMBODIMENT

The preferred multi-purpose adhesive composition of the present invention contains about 25 parts by weight of an SIS block containing 25% styrene, by weight, of the entire block copolymer; about 60 parts of a pentaerythritol ester; about 15 parts by weight of a naphthenic/paraffinic mineral oil; and 0.1 to 2.0 parts by weight of a blend of phosphite antioxidant, a hindered phenolic antioxidant and a thioester synergist, respectively.

The high styrene content SIS block copolymer component of the hot melt construction adhesives of the present invention may be one of two specific classes:

(a) An unvulcanized elastomeric block copolymer wherein the respective monomeric moieties are arranged in an alternating sequence having the general configuration S-I-S. In this first class, S is a non-elastomeric block derived from styrene and I is an elastomeric polymer block derived from isoprene. In the preferred embodiment, the total concentration of styrene in the block copolymer ranges from about 25% to about 50% of the total weight of the copolymer. Suitable styrene-isoprene-styrene block copolymers for use herein are available commercially from Enichem Americas under the tradename "Sol T". The preferred block copolymer for use in the compositions of the present invention is "Sol T 193B". Other commercially available polymers include those polymers manufactured under the trademarks "Shell RP6405", and "Dexco 506A". These copolymers are manufactured by Shell Chemical Company and The Dexco Chemical Company, respectively; and (b) A teleblock copolymer comprising molecules having at least three branches radially branching out from a central hub, each of said branches having polystyrene terminal blocks and an isoprene segment in the center. This type of block copolymer may also be described as having a branched polymerized isoprene mid-block with a polystyrene terminal block at the end of each branch. The total concentration of the styrene monomer therein also would range from about 25% to about 50%, by weight, of the entire copolymer.

It will also be recognized that mixtures of the above block copolymers may also be used as base copolymer components in the adhesives employed for use in manufacturing disposable soft goods.

It should be understood, however, that adjustment of the range of styrene, that is, the percent weight of the styrene as compared with the total weight of the S-I-S copolymer, below the lower limit of 25%, as specified herein, will produce undesireable results. In this regard, the reference to Puletti et al., U.S. Pat. No. 4,419,494 discloses the use of hot melt adhesive formulations based upon A-B-A block copolymers, and wherein the hot melt adhesives are improved with respect to their heat and plasticizer resistance by the addition of a polymeric fatty acid polyamide thereto. In this reference, the inventors suggest an operable range of A-B-A copolymers of 10-55% of the total adhesive composition.

Furthermore, the inventors in the reference to Puletti et al. disclose the use of commercially available S-I-S copolymers wherein the percentage of styrene content, as compared to the weight of the entire copolymer was less than 25%. For example, the inventors in this same reference disclose that polymers marketed by the Shell Company are desireable for this adhesive application. For example, the inventors in the reference to Puletti suggest that "Kraton 1107" and "Kraton 1111" are useful in the practice of their invention. In this regard, it should be understood that "Kraton 1107", and "Kraton 1111" have, as a percentage of the total weight of the respective copolymers, 14% and 21%, styrene, respectively.

As will become evident hereinafter, the inventors of the present invention have discovered surprising results when they employ S-I-S copolymers which have, as a percentage of the total weight of the copolymers, a styrene content in the range of about 25-50%. In particular, the inventors have discovered that the hot melt construction adhesive compositions display unusually desirable viscosities as well as novel bonding characteristics, when compared with compounds manufactured from related A-B-A copolymers such as "Kraton 1107" and "Kraton 1111" and which have less than 25% styrene, by weight, of the entire copolymers. These comparative test results will be discussed in greater detail hereinafter.

Moreover, the reference to Puletti et al. suggests that other A-B-A copolymers could be useful for formulating hot melt adhesives. In this regard, these copolymers were identified as copolymers which have, as a percentage of their total copolymer weight, a styrene content which falls within the specified range called for by the present invention, however, the suggested A-B-A copolymers were substances other than S-I-S. For example, the reference to Puletti et al. suggests the use of copolymers which are manufactured by the Shell Chemical Company and sold under the trademarks "Kraton, 1101, 1102, 1650, 1652 and 1657," as being useful for formulating hot melt adhesive compositions. As should be understood, Kraton 1101 and 1102 are styrene-butadiene-styrene (S-B-S) compounds. Experience has demonstrated that these compounds deteriorate rapidly upon the exposure of same to heat and therefore are not acceptable. Further, Kraton 1101 and 1102 have, as a percentage of their total copolymer weight, 31% and 28% styrene, respectively. With regard to Kraton 1650, 1652, and 1657, these compounds are SEBS compounds which have, as a percentage of their total copolymer weight, 29%, 29% and 13% styrene, respectively. In the case of the SEBS substances, these compounds have proved unsatisfactory inasmuch as they have poor elevated temperature resistance. Furthermore, and as will be discussed and demonstrated hereinafter, compounds which are formulated in accordance with the teachings of Puletti et al. have unsatisfactory viscosities for manufacturing purposes.

The tackifying resins which are used in the hot melt construction adhesives of the present invention are those which extend the adhesive properties and improve the specific adhesion of the block copolymer. As used herein, the term "tackifying resin" includes: (a) natural and modified rosin such as, for example, gum rosin, wood rosin, tall-oil rosin, distilled rosin, hydrogenated rosin, dimerized rosin and polymerized rosin; (b) glycerol and pentaerythritol esters of natural and modified rosins, such as, for example, the glycerol ester of pale wood rosin, the glycerol ester of hydrogenated rosin, the glycerol ester of polymerized rosin, the pentaerythritol ester of pale wood rosin, the pentaerythritol ester of hydrogenated rosin, the pentaerythritol ester of tall oil rosin and the phenolic modified pentaerythritol ester of rosin; (c) polyterpene resins having a softening point, as determined by ASTM method E28-58T, of from about 60° C. to 140° C., the latter polyterpene resins generally resulting from the polymerization of terpene hydrocarbons, such as the mono-terpene known as pinene, in the presence of Friedel-Crafts catalysts at moderately low temperatures; also included are the hydrogenated polyterpene resins; (d) copolymers and terpolymers of natural terpenes, e.g. styrene/terpene, α-methyl styrene/terpene and vinyl toluene/terpene; (e) phenolic-modified terpene resins such as, for example, the resin product resulting from the condensation, in an acidic medium, of a terpene and a phenol; (f) aliphatic petroleum hydrocarbon resins having a Ball and Ring softening points of from about 60° to 140° C., the latter resins resulting from the polymerization of monomers consisting primarily of olefins and diolefins; also included are the hydrogenated aliphatic petroleum hydrocarbon resins; (g) aromatic petroleum hydrocarbons and the hydrogenated derivatives thereof; (h) aliphatic-/aromatic petroleum derived hydrocarbons and the hydrogenated derivatives thereof. Mixtures of two of more of the above described tackifying resins may be required for some formulations. Especially preferred are pentaerythritol esters of tall-oil rosin and styrenated terpenes. These are available under the trade-names "WESTREZ 2110" and "ZONATAC 501 LITE" and which are available from Westvaco Chemical Co. and Arizona Chemical Co., respectively.

If desired, resins may be added which improve the elevated temperature resistance of the compound. These resins are materials which tend to associate with the styrene portion of the polymer.

Various plasticizing oils or extending oils also may be present in the composition of the present invention in amounts of 5 to 30 parts, and preferably from about 5 to about 25 parts, by weight, in order to provide wetting action and/or viscosity control. They include, not only the usual plasticizing oils, but also olefin oligomers and low molecular weight polymers, as well as vegetable and animal oil and derivatives of such oils. The petroleum derived oils which may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 350 and about 10,000. Suitable vegetable and animals oils include glycerol esters of the usual fatty acids and polymerization products thereof.

The petroleum derived waxes which can be used in the composition of the present invention are used to reduce the melt viscosity of the hot melt construction adhesives without appreciably decreasing their adhesive bonding characteristics. Among the useful wax diluents are: (1) low molecular weight, that is, 1000–6000, polyethylene having a hardness value, as determined by ASTM method D-1321, of from about 0.1 to 120 and ASTM softening points of from about 150° to 250° F.; (2) petroleum waxes such as paraffin wax having a melting point of from about 130° to 175° F. and microcrystalline wax having a melting point of from about 135° to 200° F., the latter melting points being determined by ASTM method D127-60; (3) atactic polypropylene having a Ring and Ball softening point of from about 120° to 160° C.; and (4) synthetic waxes made by polymerizing carbon monoxide and hydrogen such as Fischer-Tropsch wax. As should be understood, each of these wax diluents is solid at room temperature. Other useful substances include hydrogenated animal, fish and vegetable fats and oils such as hydrogenated tallow, lard, soya oil, cottonseed oil, castor oil, menhadin oil, cod liver oil, etc., and which are solid at ambient temperature by virtue of their being hydrogenated, have also been found to be useful with respect to functioning as a wax diluent equivalent. These hydrogenated materials are often referred to in the adhesives industry as "animal or vegetable waxes." Additionally, hydrocarbon oils, especially naphthenic or paraffinic process oils, may also be employed herein as the wax diluent. Optionally, these materials may be incorporated into the adhesive composition of the present invention in the form of a coating to improve the handling characteristics of the adhesive composition.

The stabilizers which are used in the hot melt construction adhesive compositions of the present invention are incorporated to help protect the otherwise vulnerable S-I-S block copolymer, and thereby the total adhesive composition, from a deleterious thermal and oxidative degradation which is frequently experienced by other similar copolymers during the manufacture and application of adhesive compositions utilizing same, as well as in the ordinary use of the final manufactured product. As should be understood, such degradation usually manifests itself by the deterioration of the adhesive composition in appearance, physical properties and performance. Among the most useful stabilizers are high molecular weight hindered phenols and multifunctional phenols, such as sulfur and phosphorous-containing phenols. In this regard, hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group is believed to retard its stretching frequency and correspondingly, its reactivity. This steric hindrance is believed to provide the phenolic compounds with its stabilizing properties. Representative hindered phenols include:

1,3,5-trimethyl-2,4,6-tris(3-5-ditert-butyl -4-hydroxybenzyl) benzene;

pentaerythritol tetrakis-3(3,5-di-tert-butyl -4-hydroxyphenyl) propionate;

n-octadecyl-3 (3,5-di-tert-butyl-4-hydroxyphenyl) propionate;

4,4'-methylenebis (4-methyl-6-tert butylphenol);

4,4'-thiobis(6-tert-butyl-o-cresol);

2,6-di-tert-butylphenol;

6-(4-hydroxyphenoxy)-2,4-bis(n-ocytlthio) -1,3,5-triazine;

2,4,6-tris(4-hydroxy-3,5-di-tert-butyl -phenoxy)- 1,3,5-triazine;

di-n-octadecyl-3,5-di-te rt-butyl-4-hydroxybenzylphosphonate;

2-(n-octylthio)ethyl-3,5-di-tert-butyl-4-hydroxy-benzoate; and sorbitol hexa-[3,3,5-di-tert-butyl-4-hydroxy -phenyl) propionate].

Especially preferred as a stabilizer is pentaerythritol tetrakis-3(3,5-di-tert-butyl -4-hydroxyphenyl) propionate.

The performance of these stabilizers may be further enhanced by utilizing, in conjunction therewith; (1) synergists such as, for example, thiodipropionate esters and phosphites; and (2) chelating agents and metal deactivators as, for example, ethylenediaminetetraacetic acid, salts thereof, and disalicylalpropylenediimine.

The hot melt construction adhesive compositions of the present invention may be formulated using any of the techniques known in the art. A representative example of the prior art procedure involves placing all of the oil and stabilizer substances in a jacketed mixing kettle, and preferably in a jacketed heavy duty mixer of the Baker-Perkins or Day type, and which is equipped with rotors, and thereupon raising the temperature of this mixture to a range of from about 250° to 350° F. As should be understood, the precise temperature to be used in this step will depend on the melting point of the particular ingredients. When the initial mixture, noted above, has been heated, the mixture is blanketed in $CO_2$ at a slow flow rate and the resins described above, are slowly added. When the resins are melted, and at the desired temperature, the block copolymer is added to the mixture. The resultant adhesive composition mixture is agitated until the block copolymer is completely dissolved. A vacuum is then applied to remove any entrapped air.

Optional additives may be incorporated into the hot melt construction adhesive compositions in order to modify particular physical properties. These additives may include, colorants, such as titanium dioxide, and fillers such as talc and clay, etc.

The invention is further illustrated by way of the several examples which follow.

EXAMPLE 1

A multipurpose adhesive composition in accordance with the teachings of the present invention was made by the general procedure described above. This adhesive composition had the following constituent elements:

| | |
|---|---|
| SIS block copolymer (25% styrene; Sol T 193B) | 25 parts |
| Pentaerythritol ester (108° C. melting point; Westrez 2110) | 60 parts |
| Naphthenic/paraffinic oil (Kaydol; Witco Chemical Company) | 15 parts |
| Phosphite antioxidant (Mark 273; Witco Chemical Company) | 0.50 parts |
| Hindered Phenolic antioxidant (Irganox; Ciba-Geigy Company) | 0.25 parts |
| Thioester synergist (Cyanox LTDP; American Cyanamid Corporation) | 0.25 parts |

The resulting hot melt construction adhesive compositions, upon testing, were found useful for multibead or multiline construction, elastic attachment and the application of a foamed waistband. It was further sprayed and extruded on various substrates and found to be generally acceptable for all intended purposes. The specific characteristics of this preferred formulation will be set forth in more particularity hereinafter.

EXAMPLE 2

A hot melt construction adhesive made in accordance with the teachings of the present invention and which was found to be especially useful for elastic attachment to a disposable article was made by the general procedure described above. Further this adhesive composition had the following constituent elements;

| | |
|---|---|
| SIS block copolymer (25% styrene; Sol T 193B) | 35 parts |
| Hydrogenated dicyclopentadiene resin (140° C. melting point; "Escorez 5340"; Exxon Chemical Company) | 40 parts |
| Aromatic Reinforcing Resin (155° C. melting point; "Endex 155"; Hercules Inc. | 10 parts |
| Naphthenic/paraffinic mineral oil (Kaydol; Witco Chemical Company) | 15 parts |
| Phosphite antioxidant (Mark 273; Witco Chemical Company) | 0.5 parts |
| Hindered phenolic antioxidant ("Irganox"; Ciba-Geigy Company) | 0.25 parts |
| Thioester synergist (Cyanox LTDP) | 0.25 parts |

Following testing, the adhesive composition, set forth above, was found to be a superior adhesive composition for attachment of elastic substrates to polyolefin materials.

Similar adhesive products were manufactured utilizing from about 10 to about 35 parts of the high styrene content SIS copolymers. In general, these products, following testing, were found acceptable for use in disposable soft goods construction. The inventors further discovered that the adhesive compositions containing the lower concentration of the SIS copolymer, within the range stated above were more suitable for general construction; and the adhesive compositions having the higher concentrations of the SIS copolymer, but still within the same stated range, were better for multi-purpose construction and elastic attachment, respectively.

EXAMPLES 3 THROUGH 12

In the following examples, various hot melt construction adhesive compositions were compounded using the method described earlier, and employing, in some instances, the commercially available A-B-A copolymers which were disclosed as useful in the patent to Puletti et al., U.S. Pat. No. 4,419,494. Following the compounding of these adhesive compositions, a number of emperical tests were employed to compare and contrast the various adhesive formulations thereby demonstrating the superior performance and unexpected results achieved by the adhesive formulations of the present invention.

In the following examples, which are summarized in graphic format, various prior art teachings are employed in several of the examples. A summary of each of the examples is set forth below:

EXAMPLE 3

A sample of adhesive which has chemical characteristics outside the lowermost range of the present invention. Example 3 utilizes an S-I-S copolymer marketed under the tradename "KRATON 1107," and which was described as useful in the reference to Puletti et al. This copolymer has, as a percentage of the total copolymer weight, 14% styrene;

EXAMPLE 4

A sample of adhesive which has chemical characteristics outside the lowermost range of the present invention. In this regard, example 4 employs a copolymer which is commercially available under the trademark "KRATON 1112" and which is manufactured by the Shell Chemical Company, and which has, as a percentage of the total weight of the copolymer, 14% styrene;

EXAMPLE 5

A sample of adhesive which has chemical characteristics which are outside the lowermost range of the present invention. Example 5 employs a copolymer which is commercially available under the trademark "KRATON 1117", and which is manufactured by the Shell Chemical Company, and which has, as a percentage of the total weight of the copolymer, 17% styrene;

EXAMPLE 6

A sample of adhesive which has chemical characteristics which are outside the lowermost range of the present invention. Example 6 employs a copolymer which is commercially available under the trademark "KRATON 1111." This copolymer, as discussed earlier has, as a percentage of the total weight of the copolymer, 21% styrene;

EXAMPLE 7

A sample of adhesive which has chemical characteristics within the range specified for adhesive compositions of the present invention. Example 7 employs a commercially available copolymer [SBS] which is marketed under the trademark "STEREON 840A" and which is sold by the Firestone Chemical Company. This copolymer has, as a percentage of the total weight of the copolymer, 43% styrene;

EXAMPLE 8

A sample of adhesive formulated within the range specified for the present invention. Example 8 employs a copolymer marketed by the Shell Chemical Company as "SHELL RP6405," and which has, as a percentage of the total weight of the copolymer, 28% styrene;

EXAMPLE 9

A sample of adhesive which is formulated within the range specified for adhesive compositions of the present invention. Example 9 employs the copolymer "SOL T 193B" and which has, as a percentage of the total weight of the copolymer, 25% styrene;

EXAMPLE 10

A sample of adhesive which is formulated within the range specified for the present invention. Example 10 employs the copolymer "DEXCO 506A" and which is marketed by the Dexco Company, and which has, as a percentage of the total weight of the copolymer, 28% styrene;

EXAMPLE 11

A sample of adhesive which is formulated within the range specified for the present invention and which employs the copolymer "STEREON 840A" and which has, as a percentage of the total weight of the copolymer, 43% styrene. This formulation is disclosed in the reference to Schmidt, Jr. et al., U.S. Pat. No. 4,526,577;

EXAMPLE 12

A sample of adhesive which is formulated with chemical characteristics within the range specified for the present invention. In the present example, a blend of KRATON 1102 (S-B-S) and KRATON 1111 (S-I-S) is employed. As should be understood, this compound was formulated in accordance with the teachings of Puletti et al. More particularly, this compound is set forth as Example 2, in Table II of Puletti et al.

Following the formulation of the adhesive compositions which are summarized above, the following tests were performed:

Viscosity. This characteristic was measured by employing conventional technology. In this regard, the viscosity of each of the adhesive formulations was measured at a temperature of 325° F. and is expressed herein in centipoise (cP). A Brookfield Thermosel was employed to determine the viscosity. The viscosity measurement was done in accordance with ASTM Method D3236-73.

Penetration. This is a test of the hardness of each of the adhesive materials. In summary, a sample of each of the adhesive materials, formulated above, was exposed to a needle which has a 200 gram load applied thereto. This needle, and the associated 200 gram weight are placed on the surface of each of the adhesives and then permitted to freefall during the test for a period of approximately five seconds. The depth of penetration of the needle is then measured and expressed in decimillimeters (dmm). The hardness test is performed at room temperature (77° F.). This hardness determination is conducted in accordance with ASTM Method D-5 as modified for use with a 200 gram weight.

Multibead Bond Strength Evaluation. In this test, a test laminate was prepared by employing an Acumeter LH-1 coating assembly and which employs a three bead multibead head. Each of the adhesives to be tested was applied directly onto a polyethylene substrate by utilizing three 0.015 inch nozzles. After allowing an open time of 0.5 seconds, a polypropylene substrate was combined with the polyethylene substrate and the two substrates were simultaneously compressed together between two rollers. In this regard, the lower compression roller was steel and the upper compression roller included a roller which had a 40 durometer synthetic rubber surface. The compression experienced by the laminate was approximately one-half bar or 7.5 pounds per square inch. The application temperature was conducted at 275° F. and the add-on, that is, the amount of adhesive per a predetermined area, was 1.5 milligrams per inch. Each of the laminations produced under the conditions, noted above, were then suspended in a fashion whereby one substrate was secured in an upper jaw of an Instron tensile tester and the second substrate was clamped in the lower jaw of same so that the jaws downward motion produced a 180° peel force. Furthermore, the laminates were oriented such that the adhesive bonds were positioned in a substantially vertical orientation. Additionally, the Instron's crosshead speed was set at a speed of approximately 12 inches per minute. This represents the peel strength of the adhesive composition. In this test, the average bond strength of 6 replicate samples were recorded.

Multibead High Temperature Evaluation. In this test, a laminate was prepared in accordance with the procedures noted immediately above. However, the laminates were bonded together by three adhesive beads which were substantially one inch long each. In this test, each of the laminates was suspended by one of the substrates from a spring clip. The bonds are then stressed by a 100 gram weight which is clipped to the other of the substrates in a 180° peel configuration. As should be understood, the laminates are positioned in a fashion wherein the adhesive beads are disposed in a substantially vertical orientation. The time is then measured until complete delamination occurs. This particular test is performed at 100° F. in a mechanical convection oven. The average of six replicate samples is reported on the chart below. This represents the oven peel strength of the adhesive composition.

Spiral Spray Bond Strength Evaluation; and Spiral Spray High Temperature Evaluation. In these two tests, a spiral spray head was mounted on the Acumeter LH-1 coater. Further the adhesives to be tested were applied through a 0.018 nozzle at an application temperature of approximately 300° F. Furthermore, in applying the adhesives, an air source was used which was heated to approximately 400° F.. The adhesives to be tested were then sprayed onto a polyethylene substrate and combined with a polypropylene substrate after an open time of approximately 0.5 seconds. Following this procedure, the laminate was compressed between steel and rubber rollers with the laminate receiving a pressure of approximately 1 bar or 15 pounds per square inch. Further, the add-on level was approximately 3.0 milligrams per linear inch. Following this procedure, these laminations were then subjected to the tests, noted above, with respect to calculating the peel strength and oven peel strength of the bonds, that is, the individual laminates were subjected to a 180° peel with an Instron tensile tester at a cross-head speed of 12 inches per minute, as well as to a test utilizing a 100 gram weight and which is performed at 100° F. in a mechanical convection oven. In this regard, six replicates of each of the laminates were tested and the average was reported in the chart, noted below.

Spiral Spray Elastic Evaluation. In this test, one spiral spray head was again mounted on the Acumeter LH-1 coater. The adhesive composition, which is to be tested, was then extruded at 300° F. through a 0.030 inch nozzle. The adhesives to be tested were sprayed onto a three-strand elastic which is backed up with a polyethylene substrate. During the process, an air temperature of approximately 400° F. was employed. After an open time of approximately 0.25 seconds, the elastic was compressed between the polyethylene substrate and a nonwoven substrate. The laminate was compressed between compression rollers which included both steel and rubber, as described earlier. The laminate experienced the compression of 1 bar or 15 pounds per square inch. The add-on level was 12 milligrams per linear inch. The elastic was previously stretched to 250%. Following these steps, the creep resistance of the laminate was determined. In this test, the laminate construction is stretched to the original length of the polyethylene substrate. Following the stretching, it is attached to a sheet of corrugated material such as paper board or the like, and the length of the original bond is measured. The assembly is then placed in a mechanical convection incubator at 120° F. Following this step, and at time intervals of 30, 60, 90, 120, 180 and 240 minutes, the bonded length is measured and the amount of delamination noted.

Results of these tests are summarized in the tables which follow:

TABLE I

| Constituent Elements | EXAMPLES | | | | |
|---|---|---|---|---|---|
| | 3 | 4 | 5 | 6 | 7 |
| Westrez 2110 | 60 | 60 | 60 | 60 | 60 |
| Zonatac 105L | | | | | |
| Kraton 1107 (14% Styrene) | 25 | | | | |
| Kraton 1112 (14% Styrene) | | 25 | | | |
| Kraton 1117 (17% Styrene) | | | 25 | | |
| Kraton 1111 (21% Styrene) | | | | 25 | |
| Stereon 840A (43% Styrene) | | | | | 25 |
| Shell RP6405 (28% Styrene) | | | | | |
| Solt 193B (25% Styrene) | | | | | |
| Dexco 506A (28% Styrene) | | | | | |
| Foral 105 | | | | | |
| Escorez 5320 | | | | | |
| Kraton 1102 | | | | | |
| Kraton 1111 | | | | | |
| Macromelt 6238 | | | | | |
| Kaydol | 15 | 15 | 15 | 15 | 15 |
| Mark 273 | 0.5 | 0.5 | 0.5 | 0.5 | 0.5 |
| Irganox 1010 | 0.25 | 0.25 | 0.25 | 0.25 | 0.25 |
| DLTDP | 0.25 | 0.25 | 0.25 | 0.25 | 0.25 |
| Viscosity at 325° F. (cP) | 10,260 | 6,475 | 3,605 | 10,363 | 5,725 |
| Penetration (dmm) | 118 | 138 | 130 | 109 | — |
| MULTIBEAD BOND STRENGTH EVALUATION | | | | | |
| Instron Peels @ 12 in/min (gm) | 842 | 1,106 | 1,051 | 820 | — |
| Oven Peel 100 gm @ 100° F. (min) | 6 | 11 | 8 | 59 | — |

TABLE I-continued

| Constituent Elements | EXAMPLES | | | | |
|---|---|---|---|---|---|
| | 3 | 4 | 5 | 6 | 7 |
| SPIRAL SPRAY BOND STRENGTH EVALUATION | | | | | |
| Instron Peels @ 12 in/min (gm) | 1,371 | 1,120 | 1,181 | 838 | — |
| Oven Peel 100 gm @ 100° F. (min) | 14 | 11 | 16 | 90 | — |
| SPIRAL SPRAY ELASTIC EVALUATION | | | | | |
| Bond Retention @ 120° F. (%) after 4 hours | 63 | 38 | 38 | 86 | 71 |

TABLE II

| Constituent Elements | EXAMPLES | | | | |
|---|---|---|---|---|---|
| | 8 | 9 | 10 | 11 | 12 |
| Westrez 2110 | 60 | 60 | 60 | | |
| Zonatac 105L | | | | 60 | |
| Kraton 1107 (14% Styrene) | | | | | |
| Kraton 1112 (14% Styrene) | | | | | |
| Kraton 1117 (17% Styrene) | | | | | |
| Kraton 1111 (21% Styrene) | | | | | |
| Stereon 840A (43% Styrene) | | | | 20 | |
| Shell RP6405 (28% Styrene) | 25 | | | | |
| Solt 193B (25% Styrene) | | 25 | | | |
| Dexco 506A (28% Styrene) | | | 25 | | |
| Foral 105 | | | | | 38.5 |
| Escorez 5320 | | | | | 20 |
| Kraton 1102 | | | | | 25 |
| Kraton 1111 | | | | | 5 |
| Macromelt 6238 | | | | | 5 |
| Kaydol | 15 | 15 | 15 | 20 | 5 |
| Mark 273 | 0.5 | 0.5 | 0.5 | 0.5 | |
| Irganox 1010 | 0.25 | 0.25 | 0.25 | 0.25 | 2 |
| DLTDP | 0.25 | 0.25 | 0.25 | 0.25 | |
| Viscosity at 325° F. (cP) | 3,530 | 4,520 | 3,040 | 1,570 | 40,900 |
| Penetration (dmm) | 86 | 95 | 87 | — | — |
| MULTIBEAD BOND STRENGTH EVALUATION | | | | | |
| Instron Peels @ 12 in/min (gm) | 969 | 1,122 | 944 | — | — |
| Oven Peel 100 gm @ 100° F. (min) | 22 | 14.5 | 52 | — | — |
| SPIRAL SPRAY BOND STRENGTH EVALUATION | | | | | |
| Instron Peels @ 12 in/min (gm) | 905 | 906 | 1,046 | — | — |
| Oven Peel 100 gm @ 100° F. (min) | 64 | 20 | 36 | — | — |
| SPIRAL SPRAY ELASTIC EVALUATION | | | | | |
| Bond Retention @ 120° F. (%) after 4 hours | 94 | 87 | 73 | 55 | — |

To better appreciate the surprising results achieved by the present invention, it should be understood that, heretofore, the prior art low styrene S-I-S compounds were not particularly useful in hot melt construction adhesive compositions for soft goods because they demonstrated an unusually high viscosity. This is shown by reference to Examples 3 and 6, above. However, and in an attempt to employ these same substances in manufacturing adhesive compositions, those skilled in the art utilized diblock substances such as S-I (Styrene-Isoprene) to reduce the viscosity to acceptable levels. While this technique reduced the viscosity, it created assorted other problems such as, for example, it made the adhesive compounds less than desireable from the standpoint of elevated temperature resistance. This is best demonstrated by referring to Examples 4 and 5, above. In those Examples, it should be understood, that the S-I-S compounds utilized in these compositions have 15% and 40% diblock, by weight, of entire copolymers, respectively. When tested, as is clear from the results, these copolymers had somewhat enhanced viscosity, (6475 and 3605 cP, respectively, as compared with, for example, Examples 3 and 6) however, their elevated temperature resistance, as expressed by bond retention, decreases to a level whereby the adhesive compounds would be completely unsuitable for elastic applications. Furthermore, it should be understood that with respect to the copolymers utilized in Example 8, 9, and 10, the percentage, by weight, of diblock present in each of these copolymers was approximately 15% for Examples 8 and 9; and 0% for Example 10. These relatively low percentages of diblock in each of these copolymers should lead those skilled in the art to conclude that these copolymers should have elevated viscosities similar to that displayed in Examples 3, and 6. However, and as shown, above, a surprising result occurs inasmuch as the viscosity drops dramatically. In the preferred practice of invention, therefore, the inventors have discovered that the S-I-S compounds useful in formulating hot melt construction adhesive of the present invention should be selected from the group of S-I-S compounds which have less than 30%, by weight of the entire copolymer, of diblock, such as S-I.

In summary, therefore, it will be noted that those samples blended with an S-I-S copolymer having a styrene concentration, as a percentage of the total copolymer weight, greater than 25%, had a much more favorable viscosity. As discussed above, this was a surprising result inasmuch as viscosity measurements for copolymers having styrene concentrations just outside the lowermost range of that specified, were nearly twofold higher. For example, in Example 6, an adhesive sample was formulated and which included a copolymer having, as a percentage of the total copolymer weight, 21% styrene. When this adhesive sample was tested, it was determined to have a viscosity of 10,363 centipoise (cP) at 325° F. However, and when an adhesive sample was formulated with the lowermost range specified for styrene as discussed above (25%), a very favorable viscosity of 5725 centipoise was achieved. Moreover, it was discovered that as the styrene concentration, as a percentage of the total copolymer weight increased, the viscosity continued to remain favorable, and in some instances decreased. This was surprising in light of the viscosity determinations for those samples which were outside the lowermost range specified (Examples 3, 4, 5, and 6). In addition to the novelty relative to the viscosity, and upon a closer evaluation of the test results, it appeared clear that hot melt construction adhesives of the present invention have generally comparable or slightly improved performance characteristics relative to adhesive compositions formulated outside the lowermost range specified, or which further were formulated in accordance with the prior art. For example, and referring to the remainder of the tests, the adhesive compositions of the present invention displayed characteristics which indicated that they could be used as multipurpose adhesives while simultaneously maintaining a low viscosity which would aid, and assist, of course, in the manufacturing process.

Moreover, an analysis of the test results reveals that the strength of the bonds of these new adhesive compositions were generally comparable to those samples outside the range specified. Additionally, it should be noted that the adhesive formulation, in accordance with the teachings of Puletti et al. (Example 12) had an unacceptably high viscosity and further could not be tested because the viscosity prevented it from being coated in the manner called for in the tests which were described earlier. Further, it will be seen that the bond strengths of the new adhesive compositions were just slightly lower, although acceptable, in the spiral spray strength evaluations. Finally, the new hot melt construction adhesives demonstrated increased strength, as compared with viscosity, when tested in the spiral spray high temperature evaluation, as well as in the elastic evaluation.

Therefore, it will be seen that the improved hot melt construction adhesives of the present invention provide a fully dependable and practical means for adhesively assembling a disposable soft good such as disposable diapers, feminine napkins or the like, and which further avoids the detriments associated with the prior art practices which includes, among others, employing several different adhesive compositions for assembling a disposable soft good. In addition to the foregoing, the improved hot melt construction adhesive compositions of the present invention show surprising and unusually desireable manufacturing viscosities when compared with the prior art.

It will be apparent to those skilled in the art that the foregoing examples have been made for the purpose of illustration and that variations may be made in proportions, procedures and material without departing from the scope of the present invention. Therefore, it is intended that this invention not be limited except by the claims which follow.

Having described our invention, what we claim as new and desireable to secure by Letters Patent of the United States is:

1. A hot melt construction adhesive suitable for disposable soft goods and wherein the hot melt construction adhesive is operable to bind a polyolefin or nonwoven substrates to at least one elastic, polyolefin, foam, or nonwoven substrate, the hot melt construction adhesive comprising:
    (a) about 15 parts to about 40 parts of a styrene-isoprene-styrene block copolymer, and wherein the styrene content of the styrene-isoprene-styrene block copolymer is 25% to 50%, by weight, of the total weight of the styrene-isoprene-styrene block copolymer;
    (b) about 40 to about 70 parts of a compatible tackifying resin selected from the group consisting of tackifying resins which include pentaerythritol esters;
    (c) about 5 parts to about 30 parts of a napthenic/paraffinic oil; and
    (d) 0.1 to 2 parts, by weight, of a phosphite antioxidant, hindered phenolic antioxidant and a stabilizer, and wherein the construction adhesive further is operable to have a melt viscosity of not greater than 6000 cP at a temperature of 325° F.

2. A hot melt construction adhesive as claimed in claim 1 and wherein the tackifying resin is any compatible resin or mixture thereof selected from the group consisting of (1) natural and modified rosins; (2) glycerol and pentaerythritol esters of natural and modified rosins; (3) polyterpene resins having a softening point as determined by ASTM method E28-58T, of from about 80° C. to 140° C.; (4) copolymers and terpolymers of natural terpenes; (5) phenolic modified terpene resins and the hydrogenated derivatives thereof; (6) aliphatic petroleum resins and the hydrogenated derivatives thereof; (7) aromatic petroleum resin and the hydrogenated derivatives thereof; and (8) aliphatic/aromatic petroleum resins and the hydrogenated derivatives thereof.

3. A hot melt construction adhesive as claimed in claim 1 and wherein the styrene-isoprene-styrene block copolymer is selected from the group of copolymers which include an unvulcanized elastomeric block copolymer, and wherein the respective monomeric moieties are arranged in an alternating sequence having the general sequence of styrene-isoprene-styrene, and teleblock copolymers having molecules wherein at least three branches radially extend outwardly from a central hub, and wherein each of the branches have polystyrene terminal blocks and an isoprene segment in the center.

4. A hot melt construction adhesive as claimed in claim 1 and wherein the napthenic/paraffinic oil is selected from the group which includes oligomers of polypropylene, polybutenes, hydrogenated polyisoprene and hydrogenated butadiene, and which have average molecular weights of about 350 to about 10,000, vegetable and animal oils including glycerol esters of fatty acid 1 and polymerization products thereof.

5. A hot melt construction adhesive as claimed in claim and wherein the Styrene-Isoprene-Styrene block copolymer is selected from the group of copolymers which have less than 30%, by weight, of diblock.

6. A hot melt construction adhesive for assemblign disposable soft goods, and wherein the hot melt construction adhesive binds a polyolefin or nonwoven substrate to at least one elastic, polyolefin, foam or nonwoven substrate, the hot melt construction adhesive consisting essentially of:

(a) about 25 parts to about 50 parts of a styrene-isoprene-styrene copolymer which is selected from the group of copolymers wherein the styrene component of the copolymer is 25% to 50%, by weight, of the styrene-isoprene-styrene copolymer selected; and has less than 30%, by weight of diblock;

(b) about 40 to about 60 parts, by weight, of a compatible tackifying resin;

(c) about 15 parts, by weight, of a plasticizing oil;

(d) about 0 to 5 parts, by weight, of a petroleum derived wax; and (e) 0.1 to 2.0 parts, by weight, of a stabilizer, and wherein the hot melt construction adhesive has a creep-resistance greater than 70%, and a viscosity of not greater than 6000 cP at a temperature of 325° F.

* * * * *

UNITED STATES PATENT AND TRADEMARK OFFICE
CERTIFICATE OF CORRECTION

PATENT NO. : 5,149,741
DATED : September 22, 1992
INVENTOR(S) : Mark D. Alper, et. al.

It is certified that error appears in the above-indentified patent and that said Letters Patent is hereby corrected as shown below:

Column 5, line 21, after the word "block" insert --copolymer--.

Column 19, line 1, delete the word --assemblign-- and insert --assembling--.

Signed and Sealed this

Ninth Day of November, 1993

Attest:

BRUCE LEHMAN

Attesting Officer

Commissioner of Patents and Trademarks